(12) United States Patent
Karakaya et al.

(10) Patent No.: US 10,813,570 B2
(45) Date of Patent: Oct. 27, 2020

(54) DEVICE AND METHOD FOR MONITORING A SUBJECT

(71) Applicant: KONINKLIJKE PHILIPS N.V., Eindhoven (NL)

(72) Inventors: Koray Karakaya, Eindhoven (NL); Maarten Petrus Joseph Kuenen, Eindhoven (NL); Declan Patrick Kelly, Eindhoven (NL); Ron Martinus Laurentius Van Lieshout, Eindhoven (NL); Marc Andre De Samber, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 88 days.

(21) Appl. No.: 15/574,019

(22) PCT Filed: May 24, 2016

(86) PCT No.: PCT/EP2016/061625
§ 371 (c)(1),
(2) Date: Nov. 14, 2017

(87) PCT Pub. No.: WO2016/193049
PCT Pub. Date: Dec. 8, 2016

(65) Prior Publication Data
US 2018/0296123 A1    Oct. 18, 2018

(30) Foreign Application Priority Data
Jul. 24, 2015   (EP) ...................... 15178219

(51) Int. Cl.
*A61B 5/08*   (2006.01)
*G01N 33/497*   (2006.01)
(Continued)

(52) U.S. Cl.
CPC .......... *A61B 5/082* (2013.01); *A61B 5/1118* (2013.01); *G01N 33/0004* (2013.01);
(Continued)

(58) Field of Classification Search
CPC ...... A61B 5/082; A61B 5/1118; G16H 40/63; G01N 33/0004; G01N 33/0067; G01N 33/497
(Continued)

(56) References Cited

U.S. PATENT DOCUMENTS 9,819,103 B2 * 11/2017 Fournier ............. H02G 15/013
2008/0146890 A1   6/2008 Leboeuf
(Continued)

FOREIGN PATENT DOCUMENTS

CN   103234883 A   8/2013
CN   204302258 U   4/2015
(Continued)

OTHER PUBLICATIONS

MicroPEM Personal Exposure Monitor. RTI International. accessed Jul. 3, 2019 (https://www.rti.org/sites/default/files/brochures/rti_micropenn.pdf).*
(Continued)

*Primary Examiner* — Nimeshkumar D Patel
*Assistant Examiner* — Jean F Morello (57) ABSTRACT

A device for monitoring the inhalation of airborne pollutant by a subject including a processor configured to determine or receive measurements of the amount of airborne pollutant around the subject and the amount of air inhaled by the subject, and to combine the measurements to determine a measure of the amount of airborne pollutant inhaled by the subject.

18 Claims, 6 Drawing Sheets

(51) Int. Cl.
G01N 33/00 (2006.01)
G16H 40/63 (2018.01)
A61B 5/11 (2006.01)

(52) U.S. Cl.
CPC ....... *G01N 33/0067* (2013.01); *G01N 33/497* (2013.01); *G16H 40/63* (2018.01)

(58) Field of Classification Search
USPC ...................................................... 73/31.02
See application file for complete search history.

(56) References Cited

U.S. PATENT DOCUMENTS

| | | | |
|---|---|---|---|
| 2008/0146892 A1* | 6/2008 | LeBoeuf | G16H 50/30 600/300 |
| 2009/0135003 A1 | 5/2009 | Charlier | |
| 2009/0265186 A1 | 10/2009 | Tarassenko | |
| 2013/0144527 A1 | 6/2013 | Kuhnreichi | |
| 2014/0031082 A1 | 1/2014 | Zishaan | |
| 2014/0303885 A1 | 10/2014 | Kamada | |
| 2014/0347663 A1* | 11/2014 | Rodes | G01N 1/2273 356/338 |
| 2015/0335834 A1* | 11/2015 | Anandhakrishnan | A61M 15/0066 128/203.12 |
| 2015/0356851 A1* | 12/2015 | Feletti | A61B 5/0002 340/539.26 |

FOREIGN PATENT DOCUMENTS

| | | |
|---|---|---|
| GB | 2420616 B | 5/2006 |
| JP | 2006047717 A | 2/2006 |
| RU | 2345795 | 2/2009 |
| WO | 2009103047 A2 | 8/2009 |
| WO | 2012069963 A1 | 5/2012 |

OTHER PUBLICATIONS

Vestbo, Jorgen (2013) "Diagnosis and Assessment"; Global Strategy for the Diagnosis, Management and Preventions of Chronic Obstructive Pulmonary Disease, Global Initiative for Chronic Obstructive Lung Disease., pp 9-17.
Sarah Laskow: "Wearable Sensors Will Measure How Much Air Pollution City Cyclists Inhale—Next City", Apr. 21, 2015, p. 1-3.
"Real-World Application of New Sensor Technologies for Air Quality Monitoring", Nov. 1, 2013, p. 8, paragraph 5, p. 24, paragraph 1.
http://en.wikipedia.org/wiki/Air_quality_index.
Samoli, E., et al. "Acute effects of air pollution on pediatric asthma exacerbation: evidence of association and effect modification." Environmental Research 111.3 (2011): 418-424.
Atkinson, Richard W., et al. "Acute effects of particulate air pollution on respiratory admissions: results from APHEA 2 project" American journal of respiratory and critical care medicine 164.10 (2001): 1860-1866.
Bigazzi, Alexander York; Figliozzi, Miguel Andres; Pankow, James F.; Luo, Wentai; and Isabelle, Lorne M., "Bicycle Facilities and the Uptake of Air Pollution by Active Travelers" (2014). Civil and Environmental Engineering Faculty Publications and Presentations. Paper 91.
Kouris, Ioannis, and Dimitris Koutsouris. "Identifying risky environments for COPD patients using smartphones and Internet of things objects." International Journal of Computational Intelligence Studies 3.1 (2014): 1-17.
By David Carruthers, CERC, EPUK, Oct. 16, 2014, Title: Enhancing the public's ability to reduce exposure to air pollution and odour through smart Dissemination of data and crowd dissemination of data and crowd sourcing.
http://www.buienradar.nl.
Sarah Laskow, "Wearable Sensors Will Measure Flow Much Air Pollution City Cyclists Inhale", Science of Cities, Apr. 21, 2015.
Bei-Bei, et al: "Inhalation Exposure Factors of Residents in a Typical Region in Northern China", Research of Environmental Sciences, vol. 23, No. 11, Nov. 2010, Abstract.
Examination Guidelines for Public Health Doctors Practice Skills "Public health Case Study of Public Health", Li Juan etc., Jan. 31, 2016, Peking Union Medical College, p. 144.

* cited by examiner

DEVICE AND METHOD FOR MONITORING A SUBJECT

This application is the U.S. National Phase application under 35 U.S.C. § 371 of International Application No. PCT/EP2016/061625, filed on May 24, 2016, which claims the benefit of International Application No. PCT/CN2015/080913 filed Jun. 5, 2015 and European Application No. 15178219.0 filed on Jul. 24, 2015. These applications are hereby incorporated by reference herein.

TECHNICAL FIELD

The invention relates to a device and method for monitoring a subject.

BACKGROUND TO THE INVENTION

Air pollution is known to have negative effects on personal health in general, and it is known that patients suffering from various respiratory tract conditions, such as asthma and chronic obstructive pulmonary disease (COPD), are susceptible to air pollution exposure. Patients exposed to high levels of air pollutants suffer from more frequent and more intense exacerbations. Once started, exacerbation requires intervention with various bronchodilators for enhancing the lung capacity, expectorants for loosening the mucus layer and expelling, and/or steroids for shortening the length and severity of exacerbations. These medications are typically given at high doses during the exacerbation period. In some severe cases oxygen therapy may be required as well, which is typically handled in hospitals.

It is in the best interest of patients to prevent exacerbations before they start, from the life quality and healthcare cost point of view. Moreover, medication intake is also positively affected from pro-active and personalized management of exacerbations before they start: administrating medications at high doses for treating exacerbations, and in severe cases the hospitalization process is rather costly as well.

Real time air pollution data is available for different cities and accessible for public use. In some cases, this data is provided via an app on a laptop or smartphone. Air quality index (AQI) is an indicator of the local air quality and is calculated by using the concentration of major air pollutants, including airborne particulate matter (e.g. fine particles less than 2.5 micrometers in diameter—PM2.5), nitrogen oxides (NOx), sulphur dioxide ($SO_2$), carbon monoxide (CO), etc. It is important to note that AQI levels depend on the air pollution and health standards for a particular country and region; e.g. AQI and associated health effects are different for China, Europe and USA. AQI and PM2.5 concentration data is available from measurement stations located in different parts of towns and cities, and the number of stations installed is constantly increasing.

Similarly, real time local traffic data is also becoming increasingly available, provided by local traffic monitoring stations and/or crowd sourced data (i.e. data supplied by individuals around a region, either manually or automatically).

In addition to the real time air pollution level and traffic load data, it is also possible to access real time information about meteorological conditions. Such information can include precipitation, wind speed, wind direction, relative humidity, sunlight (e.g. ultraviolet, UV) levels, etc.

Modern mobile devices, including smartphones, have the ability to track and trace the location information of the user through Global Positioning System (GPS) receivers and/or Wi-Fi. Data connectivity possibilities of these devices over third- or fourth-generation cellular systems also enables access to real time data about air pollution levels, the traffic load and meteorological data associated to that particular location.

Figure 1:
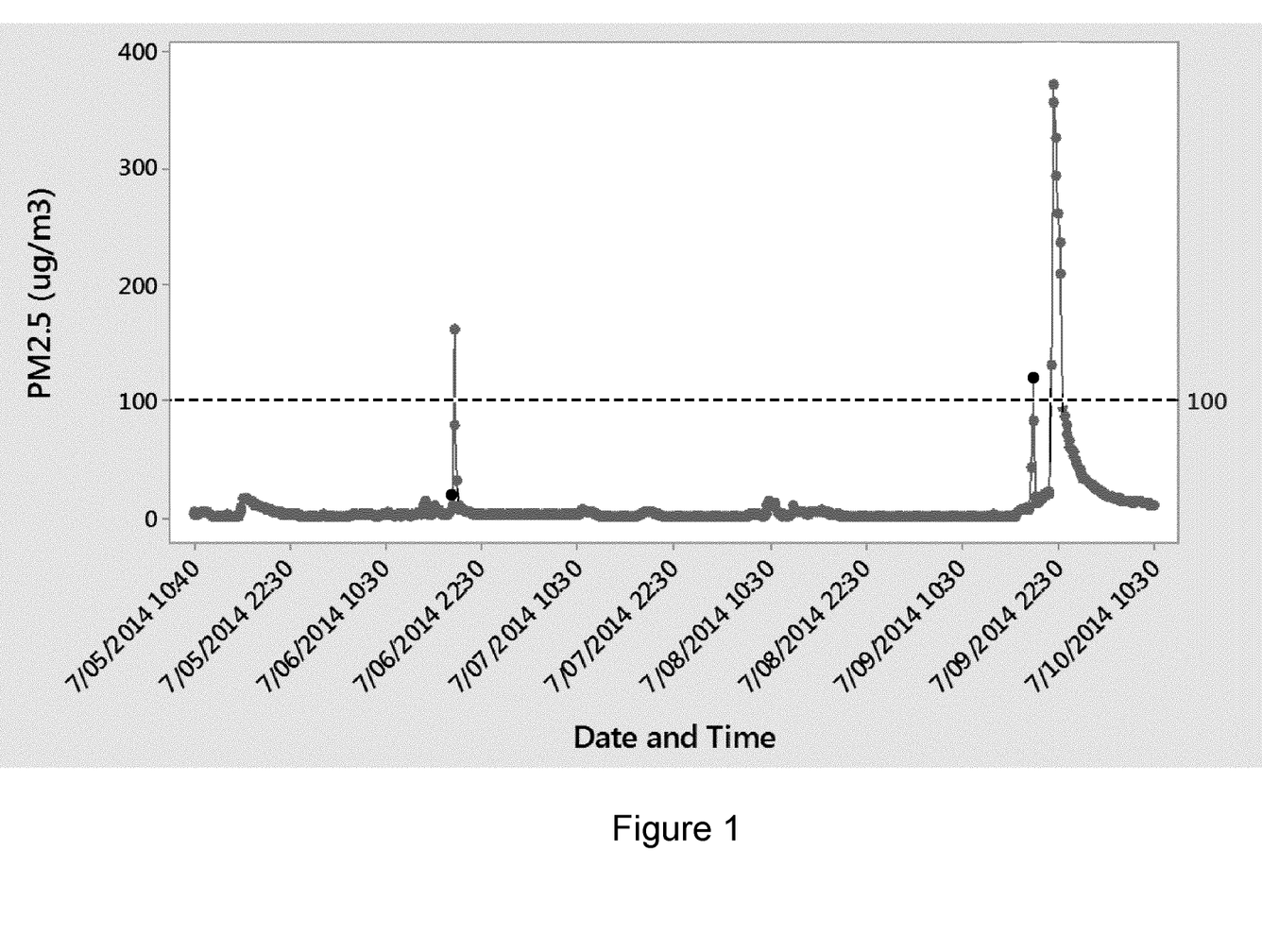
FIG. 1 is a graph illustrating the PM2.5 levels over five days in an indoor environment.

Although the distributed sensing approach for utilizing various data sources should provide good resolution of the pollution level at a given location, the actual data about particulate matter pollution levels at an individual room level indicates otherwise. The graph in FIG. 1 shows PM2.5 levels measured indoors over a five-day period. Results were collected with a professional aerosol spectrometer. The test location is Eindhoven, where typical outdoor pollution levels hardly reach to 10 $\mu g/m^3$ levels, and the annual average remains below the World Health Organization (WHO) recommendations of 15 $\mu g/m^3$. However, it can be seen that there are two significant spikes in the data (where the amount of PM2.5 substantially exceeds 100 $\mu g/m^3$) which correspond to times when food was being cooked in the room.

Thus, although various public data sources are readily available for indicating air pollution at neighborhood level, it is clear from FIG. 1 that exposure levels may easily raise to threatening levels for those who are suffering from respiratory tract conditions like COPD and asthma, even in a typical household and during regular daily life events like cooking. The importance of indoor air pollution may become more obvious considering the fact that an average person spends around 20 hours indoors, in which approximately half of it is at the home.

SUMMARY OF THE INVENTION

It has been recognized that, by itself, the level of airborne pollution may not be a sufficient measure of whether a subject is likely to suffer an exacerbation of COPD, asthma or other respiratory condition. Instead, it is the actual exposure of the subject to the airborne pollutant that is important, i.e. the amount of pollutant that enters the subject's body through inhalation. This allows the fact that different subjects in the same location may inhale different amounts of pollutant over a given time to be recognized, and provides a more personalized measure of a subject's exposure to airborne pollution. The amount of pollutant inhaled over a period of time can depend on the physical characteristics of the subject (e.g. lung capacity, breathing rate, etc.) as well as their physical activity level (which can affect the breathing rate).

Therefore a device and method are provided that enables the amount of airborne pollutant inhaled by a subject to be monitored. Various embodiments make use of the information about the amount of inhaled airborne pollutant to predict exacerbations of respiratory conditions, to provide recommendations to the subject about the use or dose of medication and/or to provide recommendations to the subject about their physical activity.

According to a first aspect, there is provided a device for monitoring the inhalation of airborne pollutant by a subject, the device comprising a processing unit configured to determine or receive measurements of the amount of airborne pollutant around the subject and the amount of air inhaled by the subject, and to combine the measurements to determine a measure of the amount of airborne pollutant inhaled by the subject. Thus, the device provides a personalized measure of the actual exposure of the subject to airborne pollution.

In some embodiments, the processing unit is configured to determine the measurement of the amount of air inhaled by the subject from a measurement or signal relating to the physical activity of the subject. In some embodiments, the device further comprises a sensor for providing measurements of the physical activity of the subject. These embodiments are advantageous as physical activity can be measured in a simple and unobtrusive manner.

In alternative embodiments, the processing unit is configured to determine the measurement of the amount of air inhaled by the subject from a measurement or signal relating to the flow rate of air during breathing by the subject. In some embodiments, the device further comprises an air flow rate sensor for measuring the flow rate of air as the subject breathes. These embodiments are advantageous as they provide a more accurate measure of the amount of inhaled pollutant.

In some embodiments, the measurement of the amount of airborne pollutant is a measurement of the amount of fine particulate matter, nitrogen oxides, sulphur dioxide, ammonia, carbon monoxide, carbon dioxide, ultra-fine particles, and/or volatile organic compounds in the air.

In some embodiments, the device further comprises a sensor for measuring the amount of airborne pollutant. In some embodiments, the processing unit is configured to receive measurements of the amount of airborne pollutant from a sensor that is separate to the device. In some embodiments, the processing unit is configured to receive measurements of the amount of airborne pollutant from a public data source.

In some embodiments, the processing unit is further configured to determine information on one or more of the geographical location of the subject, whether the subject is indoors or outdoors, whether windows and/or doors are open or closed, traffic density, and the health status of the subject, and the processing unit is further configured to use the determined information and the measurements of the amount of airborne pollutant around the subject and the amount of air inhaled by the subject to determine the measure of the amount of airborne pollutant inhaled by the subject. These embodiments have the advantage that the additional information allows the accuracy of the measure of the amount of airborne pollutant to be improved.

In some embodiments, the processing unit is further configured to provide feedback to the subject based on the determined measure of the amount of airborne pollutant inhaled by the subject.

In some embodiments, the feedback comprises information for improving the management of a respiratory condition in the subject.

In some embodiments, the feedback comprises information on medication for the subject. This embodiment has the advantage that the subject can take an appropriate amount of medication (and/or medication at an appropriate time) to avoid or reduce health problems due to the amount of inhaled pollutant.

In some embodiments, the feedback comprises information on locations the subject should be in and/or should avoid. In some embodiments, the feedback comprises information on physical activities the subject should perform and/or should not perform. These embodiments have the advantage that the risk of health problems occurring due to inhalation of airborne pollutant can be reduced.

According to a second aspect, there is provided a method for monitoring the inhalation of airborne pollutant by a subject, the method comprising determining a measurement of the amount of airborne pollutant around the subject; determining a measurement of the amount of air inhaled by the subject; and combining the measurements to determine a measure of the amount of airborne pollutant inhaled by the subject. Thus, the method provides a personalized measure of the actual exposure of the subject to airborne pollution.

In some embodiments, the step of determining a measurement of the amount of air inhaled by the subject comprises determining the measurement from a measurement or signal relating to the physical activity of the subject. In some embodiments, the measurement or signal relating to the physical activity of the subject is obtained using a physical activity sensor. These embodiments are advantageous as physical activity can be measured in a simple and unobtrusive manner.

In alternative embodiments, the step of determining a measurement of the amount of air inhaled by the subject comprises determining the measurement from a measurement or signal relating to the flow rate of air during breathing by the subject. In some embodiments, the measurement or signal relating to the flow rate of air during breathing is obtained using an air flow rate sensor. These embodiments are advantageous as they provide a more accurate measure of the amount of inhaled pollutant.

In some embodiments, the method further comprises the step of providing feedback to the subject based on the determined measure of the amount of airborne pollutant inhaled by the subject.

In some embodiments, the feedback comprises information for improving the management of a respiratory condition in the subject.

In some embodiments, the feedback comprises information on medication for the subject. This embodiment has the advantage that the subject can take an appropriate amount of medication (and/or medication at an appropriate time) to avoid or reduce health problems due to the amount of inhaled pollutant.

In some embodiments, the feedback comprises information on locations the subject should be in and/or should avoid. In some embodiments, the feedback comprises information on physical activities the subject should perform and/or should not perform. These embodiments have the advantage that the risk of health problems occurring due to inhalation of airborne pollutant can be reduced.

In some embodiments, the measurement of the amount of airborne pollutant is a measurement of the amount of fine particulate matter, nitrogen oxides, sulphur dioxide, ammonia, carbon monoxide, carbon dioxide, and/or volatile organic compounds in the air.

In some embodiments, the step of determining a measurement of the amount of airborne pollutant comprises measuring the amount of airborne pollutant using a sensor that is carried or worn by the subject. In some embodiments, the step of determining a measurement of the amount of airborne pollutant comprises obtaining a measurement of the amount of airborne pollutant from a public data source.

In some embodiments, the processing unit is further configured to determine information on one or more of the geographical location of the subject, whether the subject is indoors or outdoors, whether windows and/or doors are open or closed, traffic density, and the health status of the subject, and the processing unit is further configured to use the determined information and the measurements of the amount of airborne pollutant around the subject and the amount of air inhaled by the subject to determine the measure of the amount of airborne pollutant inhaled by the subject. These embodiments have the advantage that the additional information allows the accuracy of the measure of the amount of airborne pollutant to be improved.

According to a third aspect, there is provided a computer program product comprising a computer readable medium having computer readable code embodied therein, the computer readable code being configured such that, on execution by a suitable computer or processor, the computer or processor is caused to perform any of the methods described above.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

Figure 2:
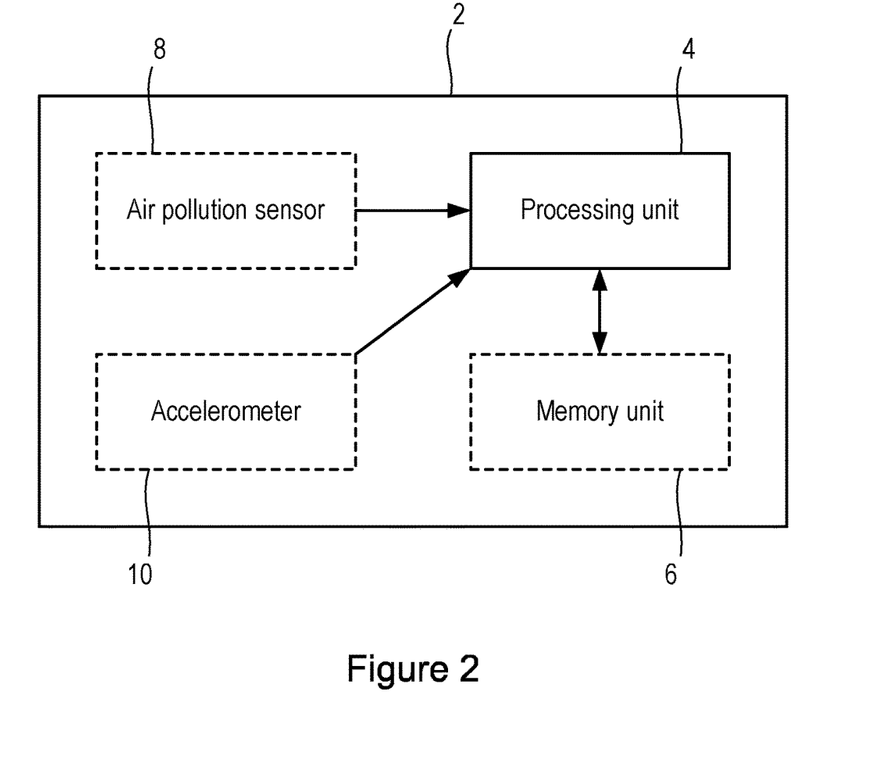
FIG. 2 is a block diagram of a device according to an embodiment of the invention.

FIG. 2 illustrates a device 2 according to an exemplary embodiment of the invention. The device 2 comprises a processing unit 4 that controls the operation of the device 2 and that determines a measure of the amount of airborne pollutant inhaled by a subject. The processing unit 4 determines the measure of the amount of airborne pollutant inhaled by the subject from an amount of airborne pollutant around the subject and an amount of air inhaled by the subject over a particular time period.

The processing unit 4 can comprise one or more processors, multi-core processors or processing modules for implementing the techniques described herein. In some embodiments, the processing unit 4 can be implemented as a plurality of processing modules, with each module being configured to perform a particular part or step of the techniques described herein.

The device 2 further comprises a memory unit 6 for storing computer readable program code that can be executed by the processing unit 4 so that the device 2 performs the method according to the invention, along with any measurements or data required to perform that method.

In some embodiments, measurements of the amount of airborne pollutant around the subject and/or measurements of the amount of air inhaled by the subject can be obtained via sensors that are separate from the device 2 (but located on or near to the subject), and they can be provided to the processing unit 4 and/or the memory unit 6 via any suitable means (e.g. wirelessly via a local wireless network (e.g. Wi-Fi, Bluetooth, etc.) or a cellular communication network, or via a wired connection). In some embodiments, the device 2 may be remote from the subject and sensors (e.g. located in the subject's home or at a healthcare facility).

Alternatively, the device 2 can include the one or more sensors for obtaining measurements of the amount of airborne pollutant and/or obtaining information for use in determining the amount of air inhaled by the subject. Thus, the device 2 can include a sensor 8 for measuring the amount of airborne pollutant and/or a sensor 10 for obtaining measurements of the amount of air inhaled by the subject (or for obtaining measurements of one or more parameters that can be processed by the processing unit 4 to determine the amount of air inhaled by the subject). The sensor(s) 8, 10 are connected to the processing unit 4.

In either case (i.e. where the sensor 8 is in the device 2 or separate), the measurements of the amount of airborne pollutant are preferably obtained by a sensor that is local or close to the subject (i.e. in the same room as the subject), and even more preferably obtained by a sensor that is worn or carried by the subject. In this way, the measurements of the amount of airborne pollutant will reflect the actual level of air pollution experienced by the subject.

The sensor 8 for measuring the amount of airborne pollutant can be any suitable sensor for measuring one or more required types of airborne pollutant. For example, the required airborne pollutant can be particulate matter (for example fine particulate matter, PM2.5), nitrogen oxides (NOx), e.g. NO or $NO_2$, sulphur dioxide ($SO_2$), ammonia ($NH_3$), carbon monoxide (CO), carbon dioxide ($CO_2$), volatile organic compounds, ultra-fine particles (e.g. particles less than 100 nanometers in diameter, such as those generated from car exhausts, cooking, smoking and burning candles), and/or any other type of airborne pollutant, and an appropriate type of sensor or sensors 8 can be provided in the device 2. Suitable types of sensors 8 are known in the art and will not be described in detail herein. In some embodiments the type or types of pollutant that the sensor 8 can measure can depend on the health condition of the subject (e.g. if there are particular types of pollutant that affect a particular health condition or particular subject).

The sensor 10 can comprise a sensor that directly measures the amount of air inhaled by the subject, and can be, for example an air flow rate sensor in a mouthpiece or face mask worn by the subject. Alternatively the sensor 10 can be a sensor that provides measurements of the breathing rate of the subject (e.g. an air flow sensor that measures when the subject is inhaling and exhaling, or an accelerometer or other motion sensor that is placed on the subject's body and that can detect accelerations caused by the movement of the chest during breathing). In these embodiments, the processing unit 4 can determine or estimate an amount of air inhaled from these measurements using information on the physical characteristics of the subject, for example the lung capacity or typical inhaled breath volume. In alternative embodiments, the sensor 10 is for obtaining measurements of the physical activity of the subject, for example an accelerometer and/or another motion sensor (such as a gyroscope, magnetometer, etc.), and the processing unit 4 can determine the amount of air inhaled from these measurements and information on the physical characteristics of the subject, for example the lung capacity, typical inhaled breath volume, etc., or by looking up a previously calculated air volume corresponding to the physical activity measurement in a look-up table. The look-up table can be specific for each individual subject, for example based on actual measurements at various physical activity levels. Alternatively, the look-up table can be compiled from the readily available data corresponding to a given subject type, which can be defined by, for example; age, gender, profession, body height, weight, body mass index, lung capacity, COPD condition level, etc.

In some embodiments, the actual amount of inhaled air can be measured by a sensor 10 in the form of an 'air sampling device' carried by or worn on the subject in which the sampled air volume changes proportionally to the physical activity level of the subject. If such a sampling device is used, it is preferred to use a pre-set value of the sampled air volume to represent the breathing volume; e.g. 1:100 volume ratio that refers to 1 unit of sampled air volume by 100 units of inhaled air volume at a given physical activity level, respectively. The air flow rate of the sampling device 10 is then adjusted during the operation proportional to the activity level of the subject, which, for example, can be detected by using various types of motion sensors (e.g. an accelerometer).

Those skilled in the art will be aware of various ways in which the physical activity or a physical activity level of the subject can be determined from accelerometer measurements. For example, the acceleration signal can be processed to determine an activity 'count', the physical activity the subject is performing (e.g. walking, running, sitting, climbing stairs, etc.), the posture of the subject, and/or any other suitable measure of the physical activity of the subject. In some embodiments the physical activity or a physical activity level can also or alternatively be given by the heart rate and/or breathing rate of the subject (which can both be measured using an accelerometer).

When the processing unit 4 has received the measurement of the amount of airborne pollutant around the subject and received or determined the amount of air inhaled by the subject, the processing unit 4 combines the measurements to determine a measure of the amount of airborne pollutant inhaled by the subject.

In some embodiments, where the amount of airborne pollutant is provided in terms of an amount per volume of air (e.g. in $\mu g/m^3$), the measure of the amount of airborne pollutant inhaled by the subject can be obtained by multiplying the amount of airborne pollutant by the amount of air inhaled by the subject over the required time period. Alternatively, where the amount of airborne pollutant and amount of air inhaled by the subject are sampled over time, the amount of pollutant inhaled by the subject can be determined by integrating the sampled amounts over time.

Where the amount of inhaled pollutant is calculated over a time period in which several measurements of the amount of airborne pollutant are obtained, the measurements of the amount of airborne pollutant can be averaged over the time period before being multiplied by the amount of inhaled air.

The amount of inhaled pollutant can be given in terms of the mass of inhaled pollutant (e.g. in g, $\mu g$, etc.), and/or converted into a form more easily understood by a subject, such as a score, or a position on a severity scale. Techniques for converting a specific measurement to a score or other form will be known to those skilled in the art, and may, for example, include comparing the determined amount to one or more threshold values.

The processing unit 4 can display the amount of inhaled pollutant to the subject or another concerned party (e.g. a family member or healthcare provider) on a display of the device 2 (which is not shown in FIG. 2), and/or the processing unit 4 can transmit the amount to another device or apparatus for use or storage by that device or apparatus.

In practical implementations, the device 2 may comprise other or further components to those shown in FIG. 2 and described above, such as a user interface that allows a subject to activate and/or operate the device 2, and a power supply, such as a battery or connection to a mains power supply, for powering the device 2. The user interface may comprise one or more components that allow a subject to interact and control the device 2. As an example, the one or more user interface components could comprise a switch, a button or other control means for activating and deactivating the device 2 and/or the process for determining the amount of pollutant inhaled by the subject. The user interface components can also or alternatively comprise a display, or other visual indicator (such as a light) for providing information to the subject about the operation of the device 2. Likewise, the user interface components can comprise an audio source for providing audible feedback to the subject about the operation of the device 2 (including audible feedback about an amount of pollutant inhaled by the subject).

In some embodiments the device 2 is a device that can easily be worn or carried by the subject, and may, for example, be in the form of a smartphone with an integrated airborne pollutant sensor 8, or an airborne pollutant sensor 8 in a separate module that can be connected wirelessly or directly attached to the smartphone. In these embodiments, the smartphone may comprise an app that controls the collection and analysis of the measurements, as well as providing the results of the analysis to the subject.

Figure 3:
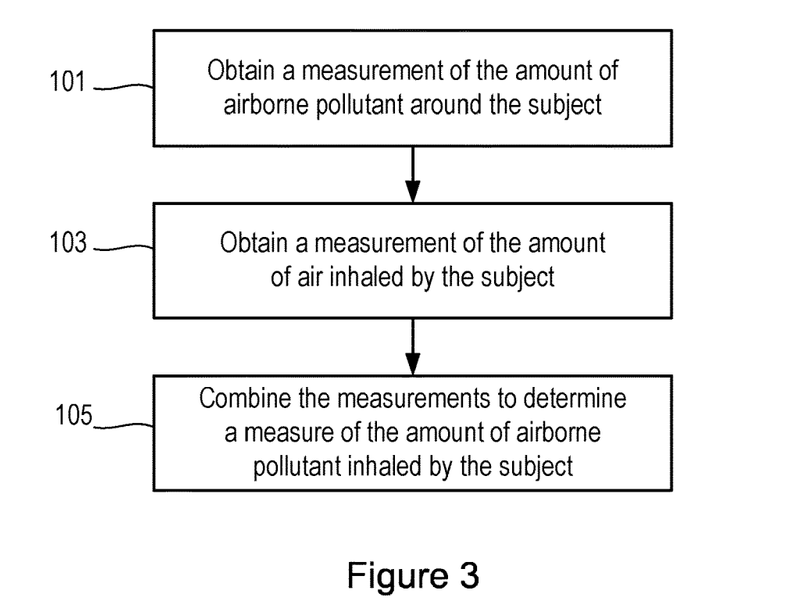
FIG. 3 is a flow chart illustrating a method according to an embodiment of the invention.

The flow chart in FIG. 3 illustrates an exemplary method of monitoring a subject according to an embodiment of the invention that can be executed by the processing unit 4. In step 101, a measurement of the amount of airborne pollutant around a subject is obtained. In step 103 (which can be performed before, at the same time, or after step 101), a measurement of the amount of air inhaled by the subject is obtained. As noted above, the measurement of the amount of air inhaled by the subject may be a direct measurement of the amount of air inhaled, or it can be an indirect measurement (such as a measure of the time and direction of air flow) or a measurement of another parameter (e.g. acceleration which can be processed to determine the type of physical activity or physical activity level) than can be used by the processing unit 4 to determine a measure of the amount of air inhaled by the subject. The measurements are then combined in step 105 to determine a measure of the amount of airborne pollutant inhaled by the subject.

In preferred embodiments of the invention, which are described in more detail below, as the measurement of the amount of pollutant inhaled by a subject provides a more subject-specific indication of the exposure to pollution than conventional measures (e.g. that are simply based on how long a subject has been in air with a certain pollution level), the measurement of the amount of inhaled pollutant can be used to improve the management of a respiratory tract condition or disorder, such as COPD or asthma. The techniques use the personal exposure to air pollution as an input, which is preferably determined from air pollution data generated by on-body (wearable) sensors, and also optionally sensors around the body (e.g. in the subject's home), and geo-localized data harvested from other environmental sensors. This context awareness leads to improvements in the personalization of the management of conditions like COPD and asthma.

In certain embodiments, the techniques described herein make use of information from several readily available data sources. These data sources can include sensors on mobile devices (e.g. smartphones); publicly available data about air pollution, traffic density and meteorological conditions, as well as 'crowd-sourced' data where individuals with similar concerns support the data coverage by sharing the status in their environment.

In some embodiments, this data can be used for providing information about a subject's personal exposure to airborne pollutant, as well as guiding subjects to optimize their daily routine to minimize the exposure to polluted air, e.g. by means of suggesting using a route through less polluted regions, or by giving advice on their physical activity level within polluted areas.

As noted above, the personal exposure to airborne pollutant can be determined from the level of airborne pollutant around the subject and a measure or indication of the amount of air inhaled by the subject. However, in some embodiments, one or more additional types of data or measurements can be obtained and used to refine the personal exposure measurement.

The additional types of data include (but are not limited to):

the geographical location of the subject: this can be determined using GPS (global positioning system), GSM (global system for mobile communications), and/or Wi-Fi based location awareness solutions;

information about whether the subject is indoors or outdoors: this can be determined from the availability/unavailability of a GPS signal (with the availability of a GPS signal indicating that the subject is outdoors, and the unavailability indicating that the subject is indoors). This information is useful to determine whether the environmental (i.e. outside) airborne pollutant may be affecting the subject. However, it should be noted that a subject may be indoors while the windows are open, in which case the indoor air pollutant concentration may be equal to the outdoor pollutant concentration;

window(s) status information (i.e. open/closed): this information can be used to compensate for the effect described above (i.e. the subject is indoors but the windows are open). This information can be received from various sensors in a connected home; e.g. window/door sensors that are part of the building security system. Another approach is to use indoor temperature and/or humidity data and compare it with publicly available meteorological information: when temperature and humidity levels measured indoors are equal or close to those outside, there is an equilibrium with outdoors and the personal exposure level can or should be estimated based on the outdoor concentration, instead of the indoor concentration;

traffic density information: this data is useful to estimate the local concentration gradients of pollutant for a given neighborhood/road. For some cities this information is already publicly available for helping city management to regulate the traffic and support drivers to optimize their route. Similar information can also be derived via crowd-sourcing: users of the system can provide input about the traffic status, or the information can be automatically derived from the population density of the system users and/or their travelling speed on a specific road (which is available via GPS);

subject's physical activity level: as well as being obtained in certain embodiments described above and used to determine the personal exposure, this information can also be obtained when there is a direct measurement of the amount of air inhaled by the subject. As noted above, an accelerometer signal can be processed to determine if a subject is walking or running, and this information can be combined with information on the speed of movement (for example obtained using GPS measurements) to enhance the precision of the information. Vertical scale movement (i.e. height changes) can be extracted or obtained from air pressure sensors or inertial sensors when the subject is indoors, or from GPS signals when the subject is outdoors. Further precision in physical activity can be achieved by using information from other sensors such as gyroscopes, or from wireless communication nodes (e.g. routers) located at different sections of buildings, etc.

air pollution information: as well as being obtained from a sensor 8 that is located near or close to the subject in the above embodiments, when the subject is outdoors air pollution information can also be obtained from the nearest air quality monitoring station. Although the pollution levels may differ at a very granulated level (e.g. differ by street, or by the particular floor in a high rise building, etc.), the air pollution level is likely to remain within a certain range for a given neighborhood. If desired, a spatial air pollution distribution over the area (e.g. town, city) can be derived from various air quality monitoring stations by taking into account the meteorological information; e.g. wind speed and direction, atmospheric pressure distribution, precipitation, etc.

When the subject is indoors, as noted above the sensor 8 may be a sensor in, or otherwise associated with, the device 2. In other or further embodiments, indoor air pollution information can be obtained by a sensor in an air purifier system and/or a sensor that is part of a stand-alone sensor unit and/or an air quality sensor that is part of a building management system.

the subject's COPD/health status: e.g. the COPD stage (0-IV) (for example the GOLD score described in Vestbo, Jørgen (2013) "Diagnosis and Assessment"; *Global Strategy for the Diagnosis, Management, and Prevention of Chronic Obstructive Pulmonary Disease*; Global Initiative for Chronic Obstructive Lung Disease. pp. 9-17); and/or the general health status (e.g. heart rate, HR, blood pressure, presence/absence of infection), both present and in the past (e.g. recovering from an infection), can affect the level of air pollution a subject can tolerate before the quality of life is decreased or exacerbations occur. This information can be gathered by means of questionnaires, health records, analysis of signals from the sensor 10 (e.g. analysis of an accelerometer signal) and/or other devices worn or carried by the subject (e.g. fitness bands, heart rate/blood pressure monitors, etc.).

It will be appreciated from the above description that the device 2 can take several different forms. In some embodiments the device 2 can be local to the subject, along with the sensors 8, 10. In these embodiments the device 2 can be implemented in a smartphone or other portable device worn or carried by the subject. In other embodiments, the sensors can be local to the subject (for example in a smartphone or other portable device worn or carried by the subject, or otherwise located near to the subject), and the functionality of the device 2 can be implemented in a local computer or a remote server.

As noted above, the calculation of the exposure of the subject to airborne pollutant (i.e. the amount of airborne pollutant inhaled by the subject) is a function of the amount of air breathed in by the subject, the level of air pollution at a given location, and the time that the subject is in the given location.

Figure 4:
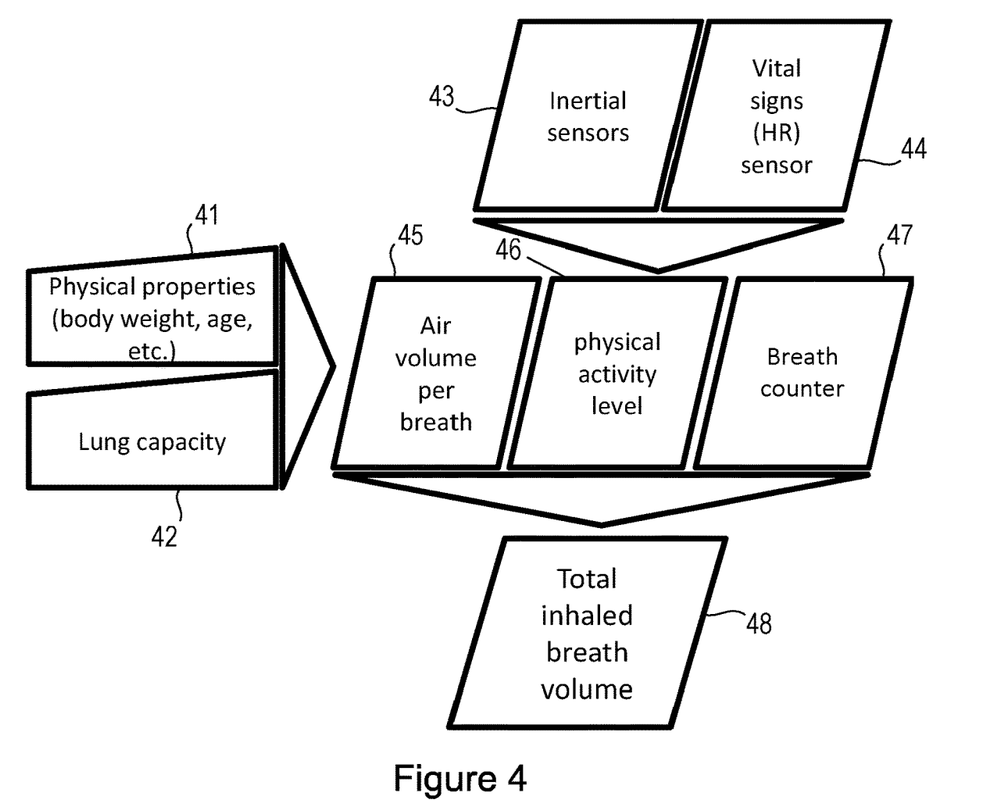
FIG. 4 illustrates an exemplary algorithm for calculating a total volume of inhaled breath.

FIG. 4 illustrates an exemplary algorithm for calculating the amount of air inhaled by a subject over a certain time period. The algorithm receives a number of different types of information as input. The more types of information that are input to the algorithm, the more accurate or reliable the output will be. Thus, the algorithm can receive information on physical properties 41 of the subject, for example information on body weight, height, age, etc., information on lung capacity 42, information from motion or inertial sensors 43 (e.g. information on the physical activity or motion of the subject) and information from vital signs sensors 44 (e.g. information on heart rate, breathing rate, etc., which can, for example, by measured using an accelerometer). The physical properties 41 and lung capacity 42 can be used to calculate a volume of air inhaled by the subject per breath 45. The information from the motion or inertial sensors 43 and vital signs 44 can be used to calculate a measure of the physical activity or physical activity level 46. The volume of air inhaled by the subject per breath 45, physical activity level 46 and (optionally) information on the number of breaths 47 (which can be obtained from a breath counter, by analysis of the motion/inertial sensor information 43 or as part of the vital signs information 44) are used to calculate the total inhaled breath volume 48. Those skilled in the art will be aware of ways in which the above calculations can be implemented, and further details are not provided herein.

Figure 5:
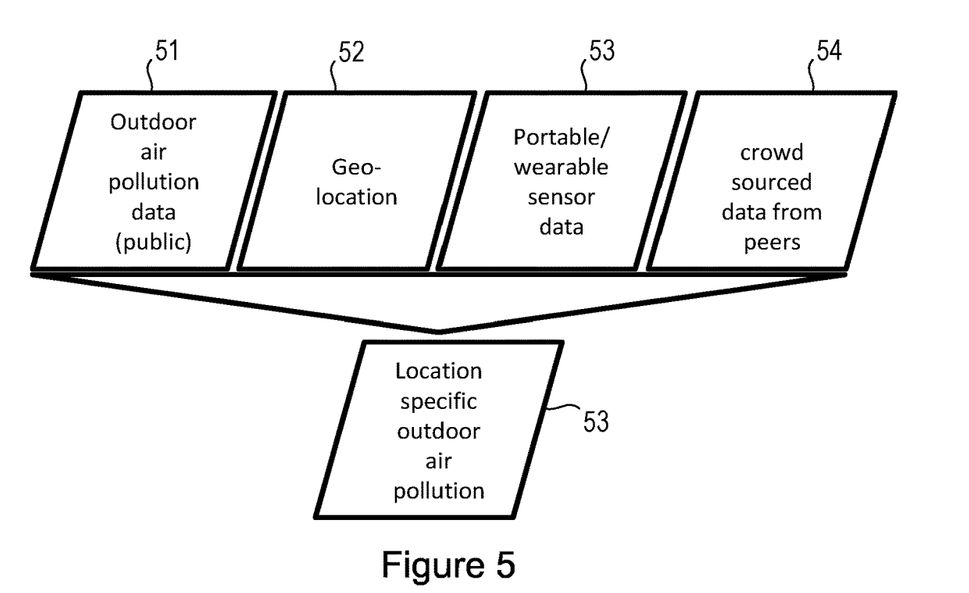
FIG. 5 illustrates an exemplary algorithm for calculating a location-specific amount of outdoor air pollution.

FIG. 5 illustrates an exemplary algorithm for calculating the amount of airborne pollutants at a given location. The algorithm receives a number of different types of information as input. The more types of information that are input to the algorithm, the more accurate or reliable the output will be. Thus, the algorithm can receive information on outdoor air pollution levels 51 (which can be obtained from publicly available sources, such as local monitoring stations), the location of the subject 52, information on pollution levels from portable or wearable sensors 53 (e.g. sensors in a smartphone, or in the device 2) and (optionally) information on pollution levels that is crowd-sourced from peers 54 (e.g. from other users of devices 2 or other types of devices and systems). The algorithm uses these sources of information 51, 52, 53 and 54 to determine a location-specific measure of the outdoor air pollution level 55. Those skilled in the art will be aware of ways in which the above calculation can be implemented, and further details are not provided herein.

Figure 6:
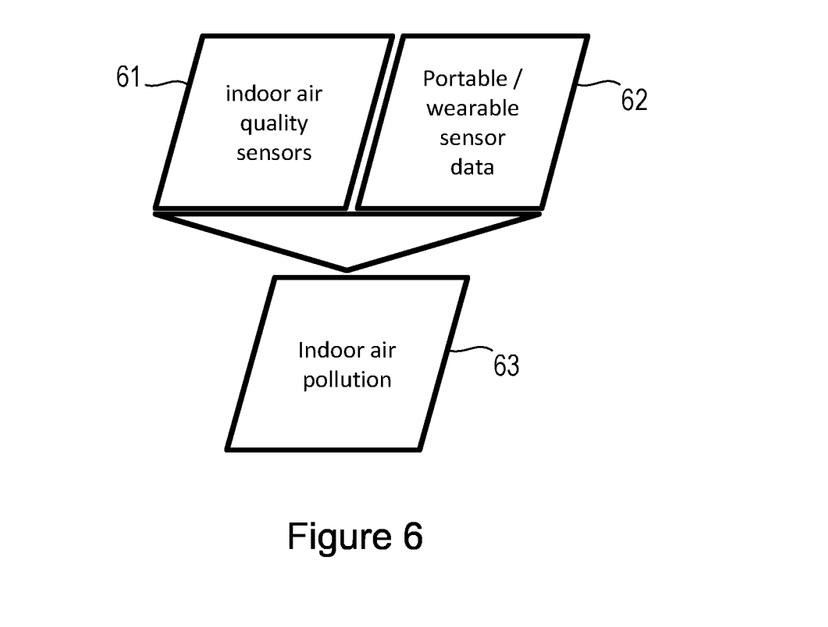
FIG. 6 illustrates an exemplary algorithm for calculating an amount of indoor air pollution.

FIG. 6 illustrates an exemplary algorithm for calculating the level of indoor air pollution at a given location. The algorithm receives a number of different types of information as input. The more types of information that are input to the algorithm, the more accurate or reliable the output will be. Thus, the algorithm can receive information from indoor air quality sensors 61 (e.g. sensors that are part of air humidification/purification devices, sensors that are part of a building monitoring system, etc.) and information from portable or wearable sensors 62 (e.g. sensors in a smartphone, or in the device 2). The algorithm uses these sources of information 61, 62 to calculate the amount of indoor air pollution 63. Those skilled in the art will be aware of ways in which the above calculation can be implemented, and further details are not provided herein.

Figure 7:
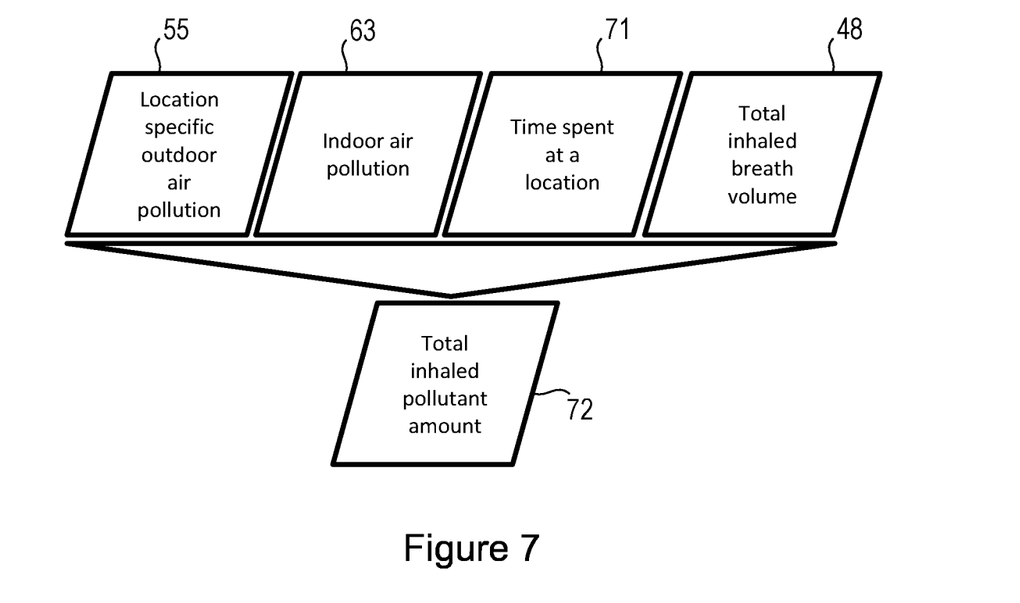
FIG. 7 illustrates an exemplary algorithm for calculating a total amount of pollutant inhaled by a subject.

Finally, FIG. 7 illustrates an exemplary algorithm for calculating the total amount of airborne pollutant inhaled by a subject. The algorithm receives the location-specific measure of the outdoor air pollution level 55, the amount of indoor air pollution 63, the total inhaled breath volume 48 and information on the time the subject has spent at the particular location 71 and uses this information to calculate the total amount of airborne pollutant inhaled by a subject 72.

In some embodiments, the device 2 can be, or be part of, a COPD management and advice system. This system can provide the subject with information on how the determined amount of inhaled airborne pollutant may affect the subject (for example provide an indication of the likelihood of an exacerbation occurring). Based on the determined amount of inhaled airborne pollutant (and an amount of airborne pollutant expected to be inhaled at current pollution and/or physical activity levels), the system may provide advice to the subject on the administering of medication to treat or reduce the risk of exacerbations occurring, and/or provide advice to the subject on changes to their physical activity level or planned physical activities. This advice can be provided via a user interface, such as a display and/or speaker(s).

As the sensitivity of a subject to pollution can be related to the severity of the subject's COPD, in some embodiments the COPD management system can be 'trained' using subject-specific data on daily activities, typical and actual exposed pollution level, the observed severity of COPD symptoms, types and dosages of regular medication, etc.

Figure 8:
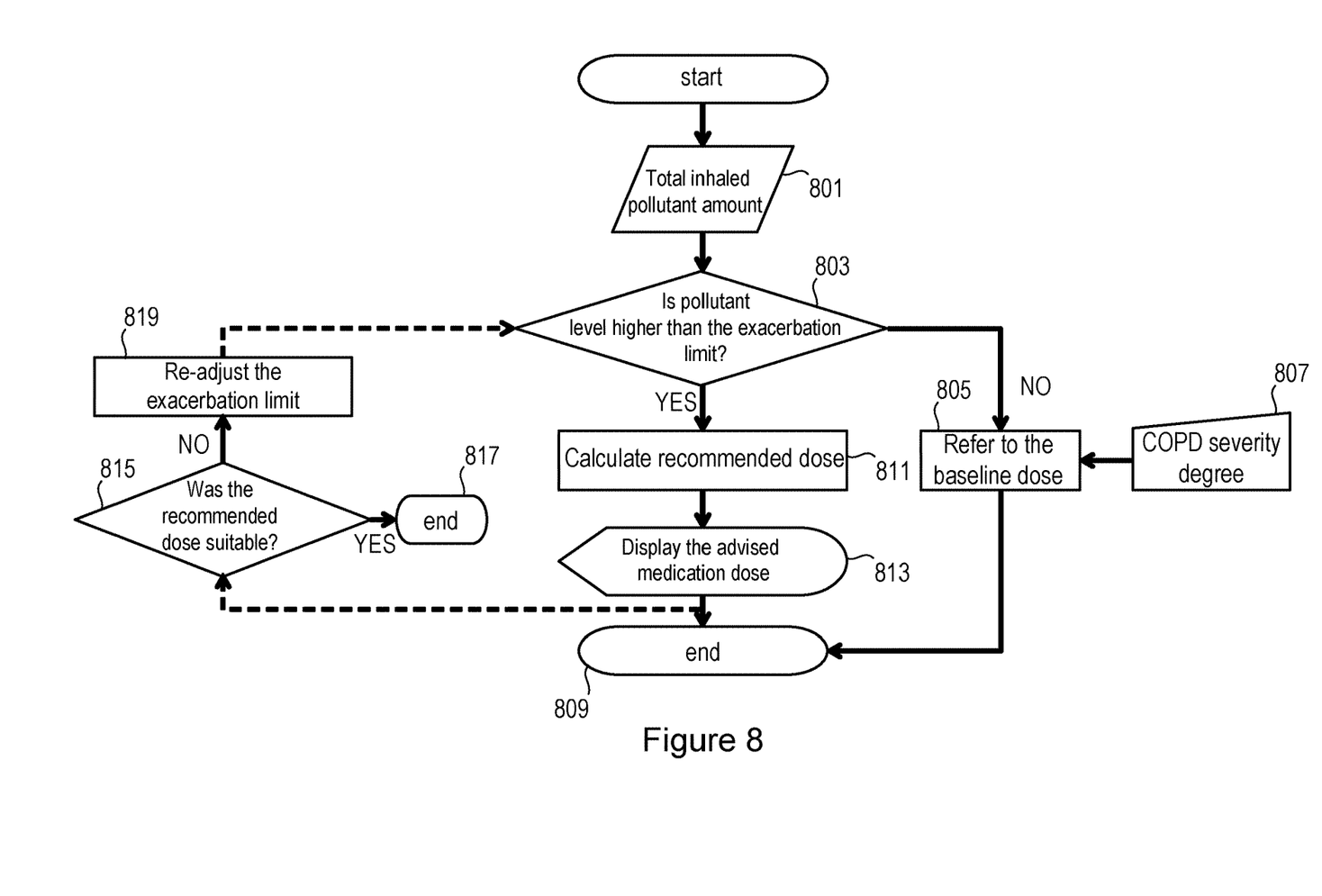
FIG. 8 is a flow chart illustrating a method of personalized exposure-aware medication dose adjustment.

An exemplary personalized exposure-aware medication dose adjustment process is shown in FIG. 8. This process considers the personalized exposure level (i.e. amount of inhaled airborne pollutant), the degree of COPD and the 'exacerbation limit', which can optionally be tailored over time by getting feedback from the subject on the actual result of the recommend dose intake.

In a first step, step 801, the total amount of inhaled pollutant is determined. This can be determined as described above. Next, in step 803, it is determined whether the pollutant level is higher than an exacerbation limit for the subject. The exacerbation limit is a value that is personal to the subject, and in particular is based on the severity of the subject's condition and/or the subject's sensitivity to air pollution. As noted below, the exacerbation limit for the subject can be adjusted based on the effectiveness of a dose of medication, in which case the exacerbation limit can initially be set to a default value (e.g. a safe low level) for the subject or a population of subjects, and adjusted from there. If the inhaled pollutant amount is lower than the limit, the method passes to step 805 in which the subject is advised to use the baseline dose for a particular medication (e.g. an inhaler). The baseline dose may have been previously determined based on the degree of severity of the subject's COPD, or determined dynamically based on the current degree of severity of the subject's COPD (step 807). After referring the subject to the baseline dose, the process ends (step 809).

If the inhaled pollutant amount is above the limit, then a recommended medication dose is calculated (step 811). Those skilled in the art will be aware of various ways in which a new dose or a change to a dose can be calculated. The new recommended dose is then displayed to the subject (step 813). In some embodiments, the process then ends (step 809).

In other embodiments, the system can receive feedback on whether the new recommended dose was suitable, and adjust the future operation of the system accordingly. Thus, in step 815 it can be determined whether the recommended dose was suitable. In some embodiments this step can comprise the subject responding to a query from the system, but in other embodiments this step can comprise the system determining this autonomously from measurements of vital signs and/or other health parameters of the subject. If the recommended dose was suitable, then the process ends (step 817). If the recommended dose was not suitable, then the exacerbation limit is adjusted (step 819) and the process returns to step 803.

In an alternative approach, the method in FIG. 8 can be used to determine whether to adjust the medication dose or the method/function used to calculate the dose of medication in addition to or instead of adjusting the exacerbation limit.

In some embodiments, the device 2 or system can also collect information on the subject's coughing frequency and/or intensity. Data on coughing can be collected to provide a historical record of cough frequency and intensity over time, location and exposed pollution level. This information is particularly useful for the identification of high risk locations, as well as monitoring the improvement/worsening in the condition over time. The coughing frequency and the intensity can be detected with devices such as an acoustic sensor, a chest strap for detecting chest movements that can be associated with coughing, etc..

Figure 9:
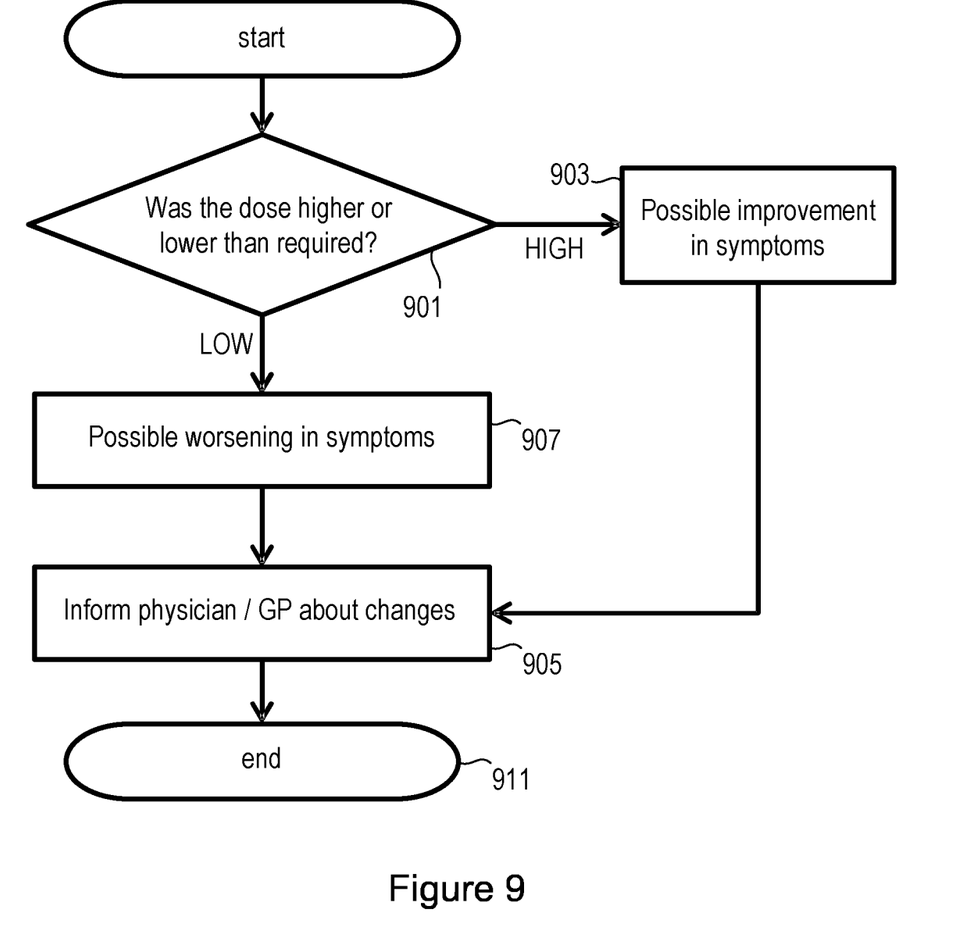
FIG. 9 is a flow chart illustrating an exemplary self-learning process.

An exemplary process illustrating a self-learning aspect of the system that is useful for providing feedback to a physician/GP is shown in FIG. 9. In a first step, step 901, it is determined whether the dose of medication was higher or lower than required. This can be determined by the subject reporting or displaying no discomfort or other symptoms due to air pollution but only side effects of the medication (in which case the dose of medication may have been higher than required) or the subject displaying increased susceptibility to air pollution (in which case the dose of medication may have been lower than required). If it is determined that the dose of medication was higher than required, there may have been an improvement in symptoms (step 903), which can be recognized through feedback from the subject and/or from improvements in the vital signs or other physiological parameters of the subject. This information can be provided to a physician or GP (step 905) so that it can be taken into account when prescribing the next course of medication. The process then ends (step 911). If it is determined that the dose of medication was lower than required, there may have been a worsening in symptoms (step 907), which, as in step 903, can be recognized through feedback from the subject and/or from improvements in the vital signs or other physiological parameters of the subject. This information can be provided to the physician or GP in step 905 so that it can be taken into account when prescribing the next course of medication.

As noted above, in some embodiments, the COPD management system can provide advice or guidance to the subject to try to avoid or minimize the excessive inhalation of airborne pollutants. One way to do this is for the system to advise the subject to avoid particularly polluted areas or locations (for example as determined from publicly available air pollution information), or to spend no longer than a set amount of time in those areas.

However, it may be the case that it is not always possible to avoid polluted areas, so the system can provide alternative advice or recommendations. For example, if excessive pollution levels are detected and/or the amount of pollutant inhaled by the subject is too high, or will be too high if they continue with the same activity level in the same location, then the system can advise the subject to do any of:

limit their physical activity level so as to minimize their total breath volume: e.g. use an escalator or lift instead of stairs, use the car instead of cycling, walking instead of running, etc.;

use a breathing mask suitable for filtering the risky pollutants (and/or clean the air canisters in a breathing mask);

move to an indoor location with air filtration/purification facilities or another location with lower pollution levels and wait until the high exposure/exacerbation risk is decreased;

advise the subject on suitable air treatment actions for the given location (e.g. open/close windows/doors when indoors, switch on an air purifier, increase fan speed of the air purifier, etc.).

Although the above management system is described with reference to COPD, it will be appreciated that the system can be used for the management of a variety of medical conditions that are affected by exposure to air pollution.

Thus a device and method are provided that enable the amount of airborne pollutant inhaled by a subject to be monitored.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A device for monitoring inhalation of airborne pollutant by a subject, the device comprising:
   a processor configured to determine or receive measurements of an amount of airborne pollutant around the subject and an amount of air inhaled by the subject, and to combine the measurements to determine a measure of an amount of airborne pollutant inhaled by the subject,
   wherein the processor configured to determine the amount of air inhaled from information on physical characteristics of the subject,
   wherein the information on physical characteristics of the subject includes a typical inhaled breath volume,
   wherein the typical inhaled breath volume is obtained from a look-table including previously calculated air volume corresponding to physical activity measurement, and
   wherein the look-table is one of specific for the subject and compiled from data corresponding to a subject type of the subject, the subject type including at least one of age, gender, profession, body height, body weight, body mass index, lung capacity, and chronic obstructive pulmonary disease (COPD) condition level.

2. The device as claimed in claim 1, wherein the processor is configured to determine the measurement of the amount of air inhaled by the subject from a measurement or signal relating to a physical activity of the subject.

3. The device as claimed in claim 2, further comprising a sensor for providing measurements of the physical activity of the subject.

4. The device as claimed in claim 1, wherein the measurement of the amount of airborne pollutant is a measurement of an amount of fine particulate matter, nitrogen oxides, sulphur dioxide, ammonia, carbon monoxide, carbon dioxide, ultra-fine particles, and/or volatile organic compounds in the air around the subject.

5. The device as claimed in claim 1, further comprising a sensor for measuring the amount of airborne pollutant.

6. The device as claimed in claim 1, wherein the processor is further configured to provide feedback to the subject based on the determined measure of the amount of airborne pollutant inhaled by the subject, wherein the feedback includes at least one of information for improving management of a respiratory condition in the subject, information on medication for the subject, information on locations the subject should be in and/or should avoid.

7. The device as claimed in claim 6, wherein the feedback comprises information on physical activities the subject should perform and/or should not perform.

8. The device of claim 1, further comprising a sensor configured to directly measure the amount of air inhaled by the subject.

9. The device of claim 8, wherein the sensor is an air flow rate sensor in a mouthpiece or a face mask worn by the subject.

10. A device for monitoring inhalation of airborne pollutant by a subject, the device comprising:
a processor configured to:
determine or receive measurements of an amount of airborne pollutant around the subject and an amount of air inhaled by the subject, and to combine the measurements to determine a measure of an amount of airborne pollutant inhaled by the subject,
determine information related to whether the subject is indoors or outdoors, whether windows and/or doors are open or closed, traffic density, and a health status of the subject, and
use the determined information and the measurements of the amount of airborne pollutant around the subject and the amount of air inhaled by the subject to determine the measure of the amount of airborne pollutant inhaled by the subject.

11. A method for monitoring inhalation of airborne pollutant by a subject, the method comprising acts of:
determining or receiving a measurement of an amount of airborne pollutant around the subject;
determining a measurement of an amount of air inhaled by the subject from information on physical characteristics of the subject; and
combining by a processor the measurements to determine a measure of an amount of airborne pollutant inhaled by the subject,
wherein the information on physical characteristics of the subject includes a typical inhaled breath volume,
wherein the typical inhaled breath volume is obtained from a look-table including previously calculated air volume corresponding to physical activity measurement, and
wherein the look-table is one of specific for the subject and compiled from data corresponding to a subject type of the subject, the subject type including at least one of age, gender, profession, body height, body weight, body mass index, lung capacity, and chronic obstructive pulmonary disease (COPD) condition level.

12. The method as claimed in claim 11, wherein the act of determining a measurement of an amount of air inhaled by the subject comprises an act of determining the measurement of the amount of air inhaled by the subject from a measurement or signal relating to a physical activity of the subject.

13. The method as claimed in claim 11, further comprising an act of providing feedback to the subject based on the determined measure of the amount of airborne pollutant inhaled by the subject.

14. The method of claim 11, wherein the act of determining a measurement of an amount of air inhaled by the subject uses a measurement or signal relating to a physical activity of the subject.

15. The method of claim 11, wherein the act of determining or receiving a measurement of an amount of airborne pollutant around the subject determines a measurement of an amount of fine particulate matter, nitrogen oxides, sulphur dioxide, ammonia, carbon monoxide, carbon dioxide, ultrafine particles, and/or volatile organic compounds in the air around the subject.

16. The method of claim 11, further comprising acts of:
determining information on one or more of the geographical location of the subject, whether the subject is indoors or outdoors, whether windows and/or doors are open or closed, traffic density, and a health status of the subject; and
using the determined information and the measurement of the amount of airborne pollutant around the subject and the amount of air inhaled by the subject to determine the measure of the amount of airborne pollutant inhaled by the subject.

17. The method of claim 11, further comprising an act of providing feedback to the subject based on the determined measure of the amount of airborne pollutant inhaled by the subject, wherein the feedback includes at least one of:
information for improving management of a respiratory condition in the subject,
information on medication for the subject,
information on locations the subject should be in and/or should avoid, and
information on physical activities the subject should perform and/or should not perform.

18. A non-transitory computer readable medium having computer readable code emodied therein which, when executed by a processor, configure the processor to perform a method for monitoring inhalation of airborne pollutant by a subject, the method comprising acts of:
determining or receiving a measurement of an amount of airborne pollutant around the subject;
determining a measurement of an amount of air inhaled by the subject from information on physical characteristics of the subject; and
combining the measurements to determine a measure of an amount of airborne pollutant inhaled by the subject,
wherein the information on physical characteristics of the subject includes a typical inhaled breath volume,
wherein the typical inhaled breath volume is obtained from a look-table including previously calculated air volume corresponding to physical activity measurement, and
wherein the look-table is one of specific for the subject and compiled from data corresponding to a subject type of the subject, the subject type including at least one of the age, gender, profession, body height, body mass index, lung capacity, and chronic obstructive pulmonary disease (COPD) condition level.

* * * * *